United States Patent [19]
Melby et al.

[11] Patent Number: 6,066,315
[45] Date of Patent: May 23, 2000

[54] AMPHOLYTE POLYMERS FOR USE IN PERSONAL CARE PRODUCTS

[75] Inventors: Allan L. Melby, Cranberry Township; Nicholas F. Vozza, Burgettstown, both of Pa.; Richard LaMar, Weirton, W. Va.; Gary F. Matz, Carnegie, Pa.

[73] Assignee: Calgon Corporation, Pittsburgh, Calif.

[21] Appl. No.: 09/159,843

[22] Filed: Sep. 24, 1998

Related U.S. Application Data

[63] Continuation of application No. 08/828,495, Mar. 31, 1997, Pat. No. 5,879,670.

[51] Int. Cl.[7] .................................................. C08F 12/30
[52] U.S. Cl. ........................................ 424/70.16; 526/287
[58] Field of Search ........................... 526/287; 424/70.16

[56] References Cited

U.S. PATENT DOCUMENTS

| | | |
|---|---|---|
| 3,986,825 | 10/1976 | Sokol . |
| 4,065,422 | 12/1977 | Lunkmark et al. . |
| 4,128,631 | 12/1978 | Lundmark et al. . |
| 4,175,572 | 11/1979 | Hsiung et al. . |
| 4,460,758 | 7/1984 | Peiffer . |
| 4,710,374 | 12/1987 | Grollier et al. . |
| 4,719,099 | 1/1988 | Grollier et al. . |
| 4,764,365 | 8/1988 | Boothe et al. . |
| 4,772,462 | 9/1988 | Boothe et al. . |
| 4,803,071 | 2/1989 | Iovine et al. . |
| 4,837,288 | 6/1989 | Peiffer . |
| 4,842,849 | 6/1989 | Grollier et al. . |
| 4,859,458 | 8/1989 | Salamone et al. . |
| 4,946,916 | 8/1990 | Peiffer . |
| 5,275,809 | 1/1994 | Chen et al. . |
| 5,296,218 | 3/1994 | Chen et al. . |
| 5,401,810 | 3/1995 | Jansma . |
| 5,415,740 | 5/1995 | Schuster . |
| 5,654,198 | 8/1997 | Carrier . |

FOREIGN PATENT DOCUMENTS

| | | |
|---|---|---|
| 0 080 976 | 9/1986 | European Pat. Off. . |
| 0 308 189 | 4/1994 | European Pat. Off. . |
| 0 308 190 | 4/1994 | European Pat. Off. . |
| 0 353 987 | 2/1996 | European Pat. Off. . |
| 2 113 245 | 7/1995 | United Kingdom . |
| 9 519 757 | 7/1995 | WIPO . |

OTHER PUBLICATIONS

Arthur R. Sykes et al., The Use of Merquate Polymers in Cosmetics, *Drug & Cosmetic Industry,* (Feb. 1980) 126(2), 62, 64, 66, 68, 136.

*Primary Examiner*—Paul R. Michl
*Attorney, Agent, or Firm*—Diane R. Meyers; Eckert Seamans Cherin & Mellott, LLC

[57] ABSTRACT

Novel conditioning polymers containing (meth) acrylamidopropyltrimethyl ammonium chloride, meth (acrylic acid) or 2-(meth)acrylamido-2-methylpropane sulfonic acid and, optionally, a $C_1$–$C_{22}$ alkyl (meth) acrylate and the use thereof in a cosmetically acceptable medium for the treatment of a keratin-containing substrate are disclosed.

5 Claims, No Drawings

6,066,315

AMPHOLYTE POLYMERS FOR USE IN PERSONAL CARE PRODUCTS

CROSS REFERENCE TO RELATED APPLICATIONS

This is a continuation of Ser. No. 08/828,495, filed Mar. 31, 1997, U.S. Pat. No. 5,879,670.

BACKGROUND OF THE INVENTION

1. Field of the Invention

The present invention relates to novel ampholyte polymers, polymer compositions and methods for using such polymers and compositions in personal care applications. In general terms, the polymers and polymer compositions of the present invention are believed to be useful in the treatment of keratin-containing substrates. Keratin substrates include, but are not limited to, animal and human hair, skin and nails.

More particularly, the instant invention relates to polymer compositions and methods for treating keratin in which a cosmetically acceptable medium is used which contains at least about 0.01% by weight of an ampholyte polymer comprising acrylamidopropyltrimethyl ammonium chloride or methacrylamido-propyltrimethyl ammonium chloride; acrylic acid, methacrylic acid, 2-acrylamido-2-methylpropanol sulfonic acid or 2-methacrylamido-2-methylpropane sulfonic acid; and, optionally, an alkyl (meth)acrylate. Preferably, the cosmetically acceptable medium is a hair care product such as a shampoo, conditioner, styling product or rinse, or a skin care product such as a cleaner, lotion or cream.

The surface properties of keratin are of interest in cosmetic science, and there has been a long-standing desire to discover ingredients which will beneficially affect the topical and bulk condition of keratinous substrates, such as hair. For example, such ingredients must have adequate adherent properties, so that they are not only adsorbed initially, but are also retained on exposure to water. This property is referred to as "substantivity", i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2–4.0. Therefore, at the pH of a typical shampoo, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos (or to skin care products such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant: cationic polymer, where the complex is least water soluble. Generally, cationic conditioners exhibit some incompatibility at these ratios. Compatibility gives a commercially more desirable clear formulation, while incompatibility leads to a haze or precipitation, which is aesthetically less desirable in some formulations.

Hair fixative properties such as curl retention are believed to be directly related to film forming properties of cationic polymers, as well as to molecular weight, with performance generally increasing with increasing molecular weight. However, the fixative properties conferred by cationic polymers generally tend to have a reciprocal relationship to other conditioning properties, i.e., good curl retention usually means that properties such as wet compatibility will suffer, and vice versa.

Surprisingly, it has been found that the instant ampholyte polymers, which comprise: a) acrylamidopropyltrimethyl ammonium chloride (APTAC) or methacrylamidopropyltrimethyl ammonium chloride (MAPTAC); b) acrylic acid (AA), methacrylic acid (MM), 2-acrylamido-2-methylpropane sulfonic acid (AMPSA) or 2-methacrylamido-2-methylpropane sulfonic acid (MAMPSA); and c) optionally, a $C_1$–$C_{22}$ straight or branched alkyl acrylate or methacrylate; are generally useful in cosmetic formulations and provide particularly improved conditioning properties to hair products. Aside from improved conditioning, as measured by combability, substantivity, flyaway and/or feel, these polymers at the same time may improve, but are generally not detrimental to, hair fixative properties such as curl retention.

In a preferred embodiment of the present invention, an effective amount of an ampholyte polymer containing AA, MAPTAC and methyl acrylate moieties is added to an anionic surfactant-containing hair or skin care product, preferably a hair care product. Thus, the polymer compositions of the present invention can be used in, inter alia, shampoos, conditioners, rinses, coloring products, bleaching products, setting lotions, blow-drying lotions, restructuring lotions, perms and straightening products.

Aside from hair care uses, skin and nail conditioning products are desired which function to improve properties such as retention of moisture, softening of the skin, attraction of air moisture, retardation of water loss, feel and reduction of skin irritations caused by contact with cosmetic ingredients. Examples of such products include detergents, lotions and soaps.

Generally, two broad areas of skin care products have been recognized as skin conditioners: emollients and humectants. Emollients generally provide improved moisture retention in the skin and plasticization/softening of the skin. Common commercial emollients are mineral oil; petrolatum; aliphatic alcohols, such as stearyl alcohol; lanolin and its derivatives; glycol stearate; and fatty acids, such as triethanolamine oleate. Humectants generally attract moisture, retard evaporation of water from the skin surface, and plasticize/soften skin. Common commercial humectants include glycerin, propylene glycol, sorbitols, and polyethylene glycols.

A desirable skin conditioner should impart at least some of the attributes of an emollient or a humectant, as well as provide improved lubricity and feel to the skin after treatment and/or reduce skin irritation caused by other components in the conditioner such as, for example, soaps, detergents, foam boosters, surfactants, and perfumes. It is known by those skilled in the art that cationic polymers may be employed as skin and nail conditioners.

At times, it is also desirable that the ingredients of skin and nail care products have adequate adherent properties, so that they are not only adsorbed initially, but are also retained on exposure to water. This property, as in hair care applications, is referred to as "substantivity", i.e., the ability of a material contacted with the keratin of skin or nails to resist removal by water rinse-off. Generally, pH's typical of use conditions, skin and nails carry a net negative charge. Consequently, cationic polymers have long been used as conditioners in nail and skin care formulations. The substantivity of the cationic polymers for negatively charged skin and nails leads to film formation that facilitates lubricity, moisturizing and feel. Two commercially used cationic polymers are Merquat® 550 (Commercially available from Calgon Corporation), a copolymer of acrylamide and dimethyldiallylammonium chloride, and Polymer JR® (Commercially available for Union Carbide), a quaternary nitrogen-containing hydroxyethyl cellulose.

The skin and nail conditioning properties of lubricity, moisturizing and feel, are related to the film forming properties of the cationic monomers, as well as to molecular weight, with performance generally increasing with increasing molecular weight.

The conditioning property improvements of the instant polymers and polymer compositions are believed to be applicable to skin and nail care products. Further, It will be appreciated that fragile or brittle nails may be strengthened or hardened, and the appearance of the nails improved, as a result of the use of the instant ampholyte polymers.

2. Brief Description of the Background Art

Keratin conditioning additives generally are of three primary types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylamino-ethylmethacrylate, and amino functional polydimethylsiloxane. Hydrolyzed animal protein has been frequently used as a keratin conditioner. Also used are natural products such as collagen and casein. Suitable quaternary ammonium compounds include such products as stearyl dimethyl ammonium chloride.

Conditioning additives comprising copolymers of dimethyldiallylammonium chloride and other monomers are well known; see, e.g., EP 308189 (with acrylamide)and EP 0 308 190 and U.S. Pat. No. 4,803,071 (with hydroxyethyl cellulose). The use of such polymers in cosmetics is also described in Sykes et al., *Drug Cosmet. Ind.*, 126(2), 62, 64, 66, 68, 136 (1980). Amphoteric betaines have also been employed in cosmetic compositions; see GB 2, 113, 245 which discloses use of betainized dialkylaminoalkyl(meth)acrylate together with a cationic polymer.

The use of polymers of dimethyldiallylammonium chloride (DMDAAC) in the treatment of keratin is also known. See, e.g., U.S. Pat. No. 4,175,572 and 3,986,825. U.S. Pat. No. 5,296,218 discloses DMDAAC-based ampholyte terpolymers containing acrylamide for hair care applications, while U.S. Pat. No. 5,275,809 discloses DMDAAC-based ampholyte terpolymers containing acrylamidomethylpropyl sulfonic acid for hair care uses.

While the use of various combinations of cationic, anionic and/or nonionic polymers as additives for hair, skin and nail conditioning compositions has been suggested heretofore, there has been no appreciation that a significant improvement in conditioning properties could be obtained by employing an ampholyte polymer of the type described herein.

For example, U.S. Pat. No. 4,859,458 discloses hair conditioning polymers containing alkoxylated nitrogen salts of sulfonic acid which may also include additional monomers that may be neutral, anionic and/or cationic. While these include acrylamide, acrylic acid and dimethyldiallylammonium chloride, there is no suggestion of the ampholyte polymers of the present invention.

EP 0 353 987 discloses polymers for water-rinsable personal care products including conditioning shampoos, comprising a cationic monomer including dimethyldiallylammonium chloride, a monomer that carries a pendant group $A_nR$ where n is 0 or a positive integer, A is ethyleneoxy and R is a hydrocarbyl group of 8 to 30 carbon atoms, and optionally a nonionic and/or an anionic monomer. However, there is no suggestion of the ampholyte terpolymers of the present invention.

U.S. Pat. No. 4,710,374 discloses compositions suitable for treating hair comprising a cationic polymer including poly(dimethyldiallylammonium chloride), and an anionic latex, but there is no suggestion of the ampholyte terpolymers of the present invention.

U.S. Pat. No. 4,842,849 discloses compositions suitable for treating keratin comprising at least one cationic polymer including poly(dimethyldiallylammonium chloride), and at least one anionic polymer containing vinylsulfonic groups, optionally copolymerized with acrylamide. The cationic polymer may be an amphoteric polymer as defined, but none of these combinations suggest the ampholyte terpolymers of the present invention.

EP 0 080 976 discloses aqueous hair-cosmetic compositions containing a surface active polymeric acrylic-based quaternary ammonium salt, a monomeric or oligomeric ammonium salt, and a surface active nonionic, anionic or zwitterionic component. The ampholyte polymers of the present invention are not suggested.

DE 4401 708 A1 discloses the use of low molecule weight MAPTAC/acrylic acid polymers in cosmetic applications. The high molecular weight (i.e., greater than 100,000) polymers of the instant invention are not disclosed or suggested.

U.S. Pat. No. 4,128,631 discloses a method of imparting lubricity to keratinous substrates such as skin or hair by contacting said substrates with a salt of 2-acrylamido-2-methylpropane sulfonic acid (AMPSA) having a molecular weight of from 1–5 million. See also U.S. Pat. No. 4,065,422. The ampholyte polymers of the present invention and their unexpected advantageous properties are not suggested.

The ampholyte polymers of the present invention and compositions containing such polymers are novel because of their unique structure, molecular weight, conditioning properties, and their general advancement of the state of the keratin conditioning art. The polymers of the present invention afford conditioning properties which are a surprising improvement over those possessed by the keratin conditioning additives in the prior art described above. Thus, for hair care, properties such as detangling, wet compatibility, wet feel, dry feel, sheen, static flyaway control, and/or curl retention are improved while, for skin and nail care, properties such strength and appearance, retention of skin moisture, softening of the skin, attraction of air moisture, retardation of skin water loss and/or, feel and reduction of skin irritations caused by contact with detergents, soaps and the like are improved.

SUMMARY OF THE INVENTION

The instant invention relates to a novel water soluble ampholyte conditioning polymers and polymer compositions for treating keratin. These polymers comprise APTAC or MAPTAC; acrylic acid, methacrylic acid, AMPSA or MAMPSA and, optionally, an alkyl acrylate or methacrylate.

The ampholyte polymer conditioning additives for hair care products disclosed herein improve wet and dry hair combability, especially detangling, wet comb and reduced static flyaway, sheen and fixative properties, especially curl retention. These ampholyte polymers, which are also effective in skin care products, may have a weight average molecular weight of from about 100,000 thousand to 10 million, and comprise (a) from at least 20 to as much as 95 mol percent of MAPTAC or APTAC; alone or in combination; (b) from at least 5 to as much as 80 mol percent of acrylic acid, methacrylic acid, AMPSA or MAMPSA, alone or in combination; (c), optionally, up to about 20 mol percent of an alkyl acrylate or methacrylate. These ampholyte polymers are added to hair or skin care product formulations in amounts ranging from about 0.01 to about 20% by weight, based on total formulation weight. They are particularly compatible with anionic surfactant-containing products such as shampoos, generally providing clear formulations without the loss of conditioning properties described above.

The present invention also relates to a method of treating keratin which comprises contacting a keratin-containing substrate with an effective amount of a cosmetically acceptable medium containing from 0.01–20%, by weight, of an instant ampholyte polymer.

DETAILED DESCRIPTION OF THE INVENTION

The instant invention is directed to novel ampholyte polymers and polymer compositions and to the use of the same in the treatment of keratin-containing substrates, particularly human skin, hair or nails.

In particular, the instant invention is directed to an ampholyte polymer prepared from or comprising: (a) up to about 99 mol % acrylamidopropyltrimethyl ammonium chloride (APTAC) or methacrylamidopropyltrimethyl ammonium chloride (MAPTAC); and (b) acrylic acid (AA), methacrylic acid (MAA), 2-acrylamido-2-methylpropane sulfonic acid (AMPSA) or 2-methacrylamido-2-methylpropane sulfonic acid (MAMPSA). Preferably, the mol ratio of a):b) in said ampholytic polymer ranges from about 20:80 to about 95:5, more preferably from about 25:75 to about 75:25. Further, the weight average molecular weight of said polymer, as determined by viscometry, is at least about 100,000, preferably from about 100,000 to about 10,000,000, more preferably from about 500,000 to about 8,000,000. Alternatively, gel permeation chromatography (GPC) with light scattering detection can be used.

Optionally, but preferably, the instant polymers additionally contain, are further comprised of or are prepared using (c) up to about 20 mol percent, preferably at least about 0.1 mol percent, of a $C_1$–$C_{22}$ straight or branched chain alkyl acrylate or methacrylate, preferably a $C_1$–$C_4$ alkyl acrylate and most preferably methylacrylate, wherein the upper mol percent of c) in the instant polymers is limited by solubility considerations. It is believed that, beyond about 20 mol % of the acrylate or methacrylate, the instant polymers become insoluble.

A more preferred molecular weight range for the instant polymers is from about 500,000 to about 8,000,000, as determined by viscosity or GPC. For example, reduced viscosity values can be used to approximate the weight average molecular weights of the instant polymers. Preferably, the mol ratio of a):b) ranges from 25:75 to about 75:25, and the preferred polymers contain at least about 0.1 up to about 20 mol % of the above-defined acrylates or methacrylates. More preferably, the instant polymers contain about 5 to about 15 mol % of the acrylate or methacrylate moiety. In the most preferred case, the alkyl acrylate or methacrylate is methyl acrylate.

The instant invention is also directed to a water soluble ampholyte polymer comprising:
a) about 20 to about 95 mol % APTAC or MAPTAC, preferably MAPTAC;
b) about 5 to about 80 mol % acrylic acid, methacrylic acid, AMPSA or MAMPSA, preferably acrylic acid; and
c) 0 to about 20 mol %, preferably 0.1 to about 20 mol %, of a $C_1$–$C_{22}$ straight or branched chain alkyl acrylate or methacrylate, preferably a $C_1$–$C_4$ alkylacrylate or methacrylate and most preferably methyl acrylate, wherein the molecular weight of said polymers is at least about 100,000.

Preferably, the instant invention is directed to a water soluble ampholyte polymer comprising:
a) about 25 to about 75 mol % APTAC or MAPTAC;
b) about 25 to 75 mol % acrylic acid or methacrylic acid; and
c) about 5 to about 15 mol % of a $C_1$–$C_{22}$ straight or branched chain alkyl acrylate or methacrylate, wherein the molecular weight of said polymer is at least about 100,000.

Further, the instant invention is directed to a method for treating a keratin-containing substrate comprising contacting said substrate with the above defined ampholyte polymer, preferably with an effective amount of said polymer or, an effective amount of a cosmetically acceptable medium comprising from about 0.01 to about 20%, preferably from about 0.1 to about 10%, by weight, based on the total weight of said medium, of an instant water soluble ampholyte polymer.

The instant invention is further directed to a cosmetically acceptable medium containing from about 0.01 to about 20%, based on the total weight of at least said medium, of one of the instant water soluble ampholyte polymers, wherein said medium is selected, inter alia, from the group consisting of shampoos, aftershaves, sunscreens, hand lotions, liquid soaps, bar soaps, bath oil bars, shaving creams, dishwashing liquids, conditioners, hair dyes, permanent waves, hair relaxers, hair bleaches, hair settings, styling gels, or shower gels. Preferably, the ampholyte polymer concentration is from about 0.1 to about 10%, based on total medium weight.

The instant invention is also directed to a method for treating a keratin-containing substrate comprising: contacting said substrate with an effective amount of an ampholyte polymer, wherein said polymer comprises:
a) about 20 to about 95 mol %, preferably about 25 to about 75 mol %, APTAC or MAPTAC;
b) about 5 to about 80 mol %, preferably about 25 to about 75 mol %, acrylic acid, methacrylic acid, AMPSA or MAMPSA; and
c) 0 to about 20 mol %, preferably about 0.1 to about 20 mol %, more preferably about 5 to about 15 mol %, of a $C_1$–$C_{22}$ straight or branched chain alkyl acrylate or methacrylate, wherein the molecular weight of said polymer is at least about 100,000.

As used herein, the term "keratin" refers to human or animal hair, skin and/or nails.

As used herein, the term "active basis" refers to a concentration of additive based on the active solids in the stock solution.

As used herein, the term "effective amount" refers to that amount of a composition necessary to bring about a desired result, such as, for example, the amount needed to treat a keratin-containing substrate relative to a particular purpose, such as conditioning.

Turning now to each of the components of the instant ampholyte polymers, the cationic component is either MAPTAC or APTAC, which may be represented as follows:

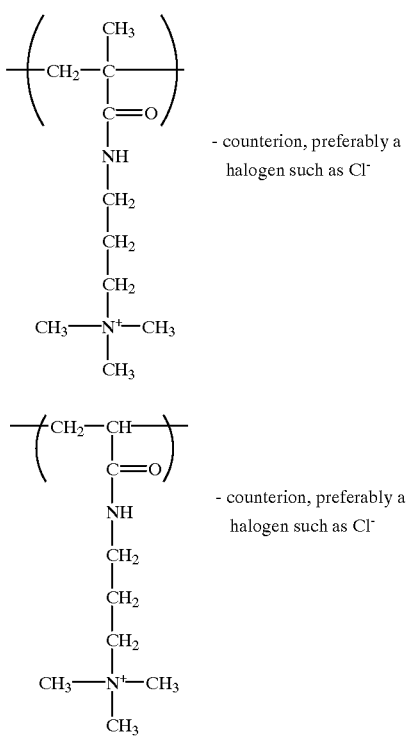

- counterion, preferably a halogen such as Cl⁻

These monomers are hydrolytically stable, and impart excellent conditioning properties to the instant polymers. MAPTAC is the preferred cationic monomer.

The cationic and anionic monomers are present in the polymers of the instant invention in an amount such that the cationic:anionic mol ratio ranges from about 20:80 to about 95:5. In such ratios, these moieties generally impart excellent conditioning properties to the instant polymers and are believed to contribute to most if not all of the hair conditioning properties mentioned above, including curl retention. These cationic monomers possess the substantivity necessary for the overall polymer to function. They also provide improved detangling, wet and dry hair combability, sheen and feel, and control of static flyaway.

The second component of the ampholyte polymers of the present invention is the anionic monomer acrylic acid (AA) or methacrylic acid (MAA), which may be represented by the following formula:

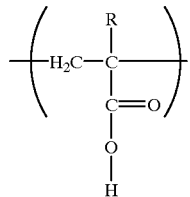

where R is H or $CH_3$. This moiety contributes to the film forming capacity of the total polymer and thus improves curl retention. In amounts as little as 5 mol percent, the acrylic acid measurably improves the compatibility of the overall polymer with anionic surfactant(s) in typical shampoo. It has also been found that AA or MAA in combination with MAPTAC/APTAC generally improves conditioning properties over conventional ampholyte polymers. This result is unexpected, and is another indication of the unexpected properties of the ampholyte polymers of the present invention.

Additionally, 2-acrylamido-2-methylpropane sulfonic acid (AMPSA) or 2-methacrylamido-2-methylpropane sulfonic acid (MAMPSA), preferably AMPSA, can be used as component (b), alone or in combination with acrylic acid or methacrylic acid. These monomers are represented as follows:

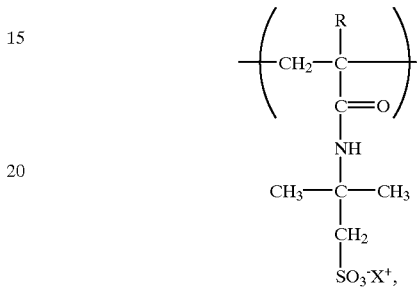

wherein R=H or $CH_3$ and X=suitable salt forming cation.

The third and optional but preferred mer unit of the instant invention is an alkyl acrylate or methacrylate represented as follows:

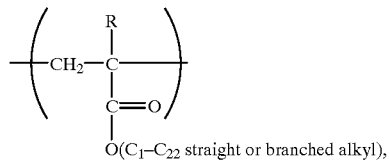

wherein R = H or $CH_3$

Preferably, this mer unit is a $C_1$–$C_4$ alkyl acrylate or methacrylate, acrylates being more preferred and with methyl acrylate being most preferred. These monomer units impart surprising and unexpected conditioning properties to the MAPTAC/AA-type copolymers of the instant invention, which are improvements over conventional ampholyte conditioning polymers in their own right.

The instant polymers may be prepared by conventional solution polymerization techniques, as indicated below and in the Examples. Thus, to prepare the instant polymers the appropriate weights for the desired mol %'s of APTAC/MAPTAC and acrylic acid or other anionic monomers are charged to a glass reactor equipped with a stirring means. The desired amount of alkyl acrylate or methacrylate is then added to the reactor with vigorous stirring to give the desired total monomer concentration, which is generally about 10–25% by weight. The monomer mixture may then be adjusted to a pH of about 3.0 to about 6.5 with dilute NaOH, heated to about 55° C., and purged with nitrogen for at least thirty minutes. Polymerization is then initiated by adding about $5 \times 10^{-2}$ mol % of sodium persulfate and about $2.4 \times 10^{-3}$ mol % of sodium bisulfate. After the peak exotherm is reached, additional dilution water and sodium bisulfite are added to scavenge any residual monomer and to dilute the final product to 4–8% polymer solids.

The preferred terpolymers, which can be prepared by this technique, are represented as follows:

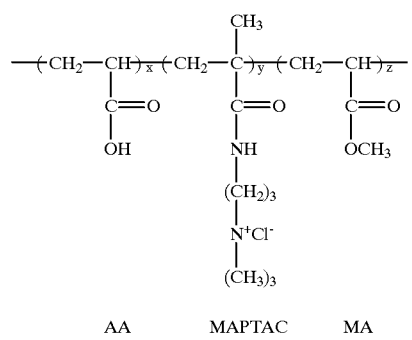

wherein x, y, and z represent mol %'s.

Representative of the best mode known to the inventors are polymers wherein the mol percentages of MAPTAC/AA/MA are 45/45/10 and such polymers are added to a cosmetically acceptable medium at a concentration of from about 0.1 to about 10%, by weight, based on total medium weight. Methods of adding the instant ampholyte polymers to a cosmetically acceptable medium are well known to those familiar with the art. The best mode also entails use of an effective amount of the polymer-containing medium in the treatment of a keratin-containing substrate, preferably human skin or hair. Methods of using such compositions are well known in the art.

The molecular weight of the ampholyte polymers of the present invention may be within the broad range of greater than about 100,000, preferably from about 100 thousand to about 10 million, and more preferably from about 500,000 to 8 million.

Reduced viscosity (dl/g) may be used as an approximate measure of the weight average molecular weight of the ampholyte polymers of the present invention. The values shown herein represent a capillary viscosity measured with Ubbelhhde Capillary Viscometer at 0.05% concentration of polymer in a 1M NaCl solution, pH 7, at 30° C. The resulting molecular weight value is calculated in accordance with methods well known in the art.

The ampholyte polymers of the present invention are used in compositions for treating hair, skin or nails by incorporating them in a cosmetically acceptable medium used to treat hair, skin or nails in amounts of about 0.01 to about 20%, on an active polymer basis, based on the total weight of said medium, and preferably in an amount of from about 0.1 to about 10% active polymer based on total medium weight.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlohydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or hair fibers, preservatives, sequestering agents, thickeners, silicones, softeners, foam synergistic agents, foam stabilizers, sun filters, peptising agents and also anionic, non-ionic, cationic or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic or amphoteric surface-active agents typically in an amount from 3–50% by weight, preferably 3–20%, and their pH is general in the range of 3 to 10.

A list of the surface-active agents which can be used according to the invention is given U.S. Pat. Nos. 4,240,450; 4,445,521 and 4,719,099.

Another preferred embodiment consists of use in the form of a rinsing lotion to be applied mainly before or after shampooing. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is generally 0.05 to 15% by weight. If the compositions are presented in the form of a styling lotion, shaping lotion, or setting lotion, they generally comprise, in aqueous, alcoholic or aqueous-alcoholic solution, the ampholyte polymers defined above.

If the compositions of the instant invention are intended for use in the dyeing of keratin fibers, and in particular human hair, they generally contain at least one oxidation dyestuff precursor and/or one direct dyestuff, in addition to the ampholyte terpolymer. They can also contain any other adjuvant normally used in this type of composition.

The pH of the dyeing compositions is generally 7 to 11 and can be adjusted to the desired value by adding an alkalizing agent.

The compositions according to the present invention can also be used for waving or straightening the hair. In this case, the composition generally contains, in addition to the instant ampholyte polymer, one or more reducing agents and, if appropriate, other adjuvants normally used in this type of composition; such compositions are intended for use conjointly with a neutralizing composition.

EXAMPLES

The following examples further define the instant inventions. They are not intended, however, to limit these inventions in any way.

In several of the following examples, wet comb and detangling work tests were performed. In many of these tests, the instant polymers were evaluated in the formulations described below. Wet comb and detangle tests were run on a mini tensile tester using lab-made hair swatches. These procedures are well known to skilled practitioners.

| SHAMPOO #1 | | |
|---|---|---|
| INGREDIENTS | INCI NAME | % WW |
| Standapol A | Ammonium lauryl sulfate | 7.50 |
| Standapol EA-3 | Ammonium laureth sulfate | 17.50 |
| Tegobetaine L-7 | Cocamidopropyl betaine | 5.0 |
| Monamid 1113 | Cocamide DEA | 3.0 |
| Polymer of instant invention or Gafquat ® | | 0.26 (active polymer) |
| Tween 20 | Polysorbate 20 | 1.00 |
| Sodium Chloride | Sodium Chloride | 0.75 |
| Glydant | DMDM hydantoin | 0.20 |
| Citric Acid | Citric Acid | q.s. to pH 6* |
| Water, D.I. | Water | q.s. to 100 |

*q.s. refers to quantity sufficient

| SHAMPOO #2 | | |
|---|---|---|
| Ingredients | INCI NAME | % WW |
| Tegobetaine L-7 | Cocamidopropyl betaine | 8.00 |
| Monaterix CDX-38 | Disodium cocoamphodiacetate | 8.00 |
| Bio-Terge AS-40 | Sodium C14–16 olefin sulfonate | 25.00 |
| Water, D.I. | Water | q.s. to 100 |
| Polymer of instant invention or Gafquat ® | | 0.26 (active polymer) |
| Ammonium Chloride | Ammonium Chloride | 0.50 |
| Glydant | DMDM hydantoin | 0.20 |
| Patlac LA | Lactic acid | q.s. to pH 6.0 |

| CONDITIONER | |
|---|---|
| Ingredients | % WW |
| Deionized Water | q.s. to 100 |
| Propylene Glycol | 2.0 |
| Polymer of instant invention or Gafquat ® | 3.0 |
| Adol 52[1] | 2.0 |
| Polawax[2] | 2.5 |
| Brij 35[3] | 1.0 |
| Blandol[5] | 1.0 |
| Superfine Lanolin[4] | 0.5 |
| Fragrance, preservative and color | q.s. |

Indexed conditioner ingredients commercially available from:
1. Sherex Chemical Company
2. Croda, Inc.
3. ICI Americas
4. Fanning Corporation
5. Witco—Sonneborn Div.

Example 1

Preparation of a 45/45/10 M/M/M Terpolymer of AA/MAPTAC/Methylacrylate

A 45/45/10 M/M/M terpolymer of acrylic acid/MAPTAC and methyl acrylate was prepared as follows:

1. Zeolite softened water, acrylic acid, and MAPTAC (Items 1, 2 and 3 in Table 1, below) were added to a glass-lined reactor in the amounts shown, and stirred until uniform.

2. Methyl acrylate monomer (Item 4) was then added to the reactor.

3. The mix temperature was held below 30° C., and the reactor was purged with nitrogen for 45 minutes.

4. After 45 minutes, the purge rate was reduced, and the mix was heated to 52±1° C. This purge rate was continued until the completion of Step 12.

5. V-501 $(2,2^1$-azobis (2-amidino propane) dihydrochloride) was slurried in water (Items 5 and 6) in a separate mix container.

6. A V-50 $(4,4^1$-azobis (4-Cyanovaleic acid)) solution in water (Items 7 and 8) was prepared in another mix tank. Steps 5 and 6 were completed during the purge and heat up.

7. The V-501 slurry was added to the reactor followed by the V-50 solution.

8. After a brief period, the reaction admixture began to exotherm, peaking at about 90–95° C. after about one hour.

9. The reaction admixture was held at the peak temperature for one hour. After one hour, water (Item 9) was added and mixed for 30 minutes or until the reaction admixture was uniform. The temperature of the reaction admixture was reduced to 70–75° C. during the dilution step.

10. Caustic (Item 10) and water (Item 11) were mixed and added to the reactor over a 30-minute period, holding the temperature below 75° C.

11. This reaction admixture was held for 15 minutes, and the temperature increased to 80–85° C.

12. Sodium bisulfite solution was added (Item 12) over 25–35 minutes at 80–85° C. It was then mixed for 30 additional minutes and the nitrogen purge was turned off. Cooling to below 50° C. then occurred.

13. Sodium benzoate (Item 13) and water (Item 14) were mixed, and added to the reactor. This admixture was stored until uniform.

14. The batch was cooled to less than 50° C. and decanted into a suitable container.

The resulting polymer, which represents the best mode known to the inventors, had a weight average % molecular weight of about $1.1 \times 10^6$, as determined by viscosity. The polymers comprised 45 mol % AA, 45 mol % MAPTAC and 10 mol % methylacrylate.

TABLE 1

AA/MAPTAC/MA Terpolymer 45/45/10 m/m/m

| ITEM | NAME | WEIGHT % | POUNDS/BATCH |
|---|---|---|---|
| 1 | Zeolite Softened Water | 31.508 | 315.08 |
| 2 | Acrylic Acid, % active | 4.664 | 46.64 |
| 15 | MAPTAC, 50% active | 28.312 | 283.12 |
| 4 | Methyl Acrylate, % active | 1.228 | 12.28 |
| 5 | V-501 | 0.014 | 0.14 |
| 6 | Soft water | 0.024 | 0.24 |
| 7 | V-50 | 0.042 | 0.42 |
| 20 | Soft water | 0.240 | 2.40 |
| 9 | Soft water | 29.812 | 298.12 |
| 10 | Caustic soda, 50% | 1.200 | 12.00 |
| 11 | Soft water | 1.200 | 12.00 |
| 12 | Sodium Bisulfite Solution, 38% | 0.956 | 9.56 |
| 253 | Sodium benzoate | 0.200 | 2.00 |
| 14 | Soft Water | 0.600 | 6.00 |
| | TOTAL FEED | 100.000 | 1000.00 |
| | EXPECTED PRODUCT AT 100% YIELD | 100.000 | 1000.00 |

Examples 2–14

Additional ampholyte polymers were prepared using the general procedure of Example 1. Results are shown in Table 2 below along with the wet comb and detangle response vs. a no polymer control and Gafquat® HS-100, a commercially available conditioner. Wet comb and detangle tests were run in a mini tensile tester using lab made 2.2 g bleached hair. Polymer solids were 0.26% in Shampoo #1.

polymer control and a corresponding amount of a commercially available conditioner in a typical shampoo formulation (shampoo # 1). Results are shown in Table 3 below.

TABLE 3

| Example # | Composition (mol %) | Reduced Viscosity | Detangling (mJoules) | Wet Comb (mJoules) |
|---|---|---|---|---|
| 15 Control - no polymer | — | — | 365 | 219 |
| 16 Gafquat® HS-100* | — | — | 266 | 67 |
| 17 | 50/50 AA/APTAC | 5.2 | | 59 |
| 18 | 45/45/10 AA/APTAC/MA | 5.8 | 247 | 35 |
| 19 | 45/45/10 AA/MAPTAC/MA | 3.8 | 433 | 32 |
| 20 | 40/40/20 AA/MAPTAC/MA | 3.8 | 246 | 35 |
| 21 | 40/40/20 AA/APTAC/MA | 6.0 | 288 | 40 |

*Gafquat® HS-100 is commercially available from International Specialty Products.

Example 22

The polymer of Example 17 (45/45/10 AA/MAPTAC/MA) was tested in the three cosmetically acceptable mediums described above, i.e., Shampoo #1, Shampoo #2 and the

TABLE 2

| Ex. # | Mol % | Initiaton Temp ° C. | Peak Temp ° C. | Temp Rise ° C. | Final pH | Reduced Viscosity d/gm | Charge | Wet Comb Response | Detangle Response |
|---|---|---|---|---|---|---|---|---|---|
| 2 | 35/45/20 AA/MAPTAC/MA | 52 | 82 | 30 | 4.5 | 3.6 | +10% ionic charge | 43 | 143 |
| 3 | 52.5/42.5/5 AA/MAPTAC/MA | 53 | 77 | 24 | 4.8 | 3.2 | −10% ionic charge | 48 | 136 |
| 4 | 42.5/52.5/5 AA/MAPTAC/MA | 52 | 76 | 24 | 4.7 | 3.3 | +10% ionic charge | 50 | 115 |
| 5 | 45/35/20 AA/MAPTAC/MA | 52 | 80 | 28 | 4.8 | 3.7 | −10% ionic charge | 41 | 216 |
| 6 | 50/50 AA/MAPTAC | 52 | 79 | 27 | 4.8 | 3.4 | copolymer 0% charge | 53 | 206 |
| 7 | 42.5/52.5/5 AA/MAPTAC/MA | 52 | 79 | 27 | 4.7 | 3.1 | +10% ionic charge | 49 | 135 |
| 8 | 45/35/20 AA/MAPTAC/MA | 52 | 91 | 39 | 4.1 | 3.7 | −10% ionic charge | 44 | 218 |
| 9 | 52.5/42.5/5 AA/MAPTAC/MA | 52 | 89 | 37 | 4.2 | 3.4 | −10% ionic charge | 47 | 135 |
| 10 | 35/45/20 AA/MAPTAC/MA | 52 | 85 | 33 | 4.2 | 3.6 | +10% ionic charge | 44 | 117 |
| 11 | 47.5/47.5/5 AA/MAPTAC/SMA* | 52 | 82 | 30 | 2.4 | 2.5 | 0% | — | — |
| 12 | 47.5/47.5/5 AA/MAPTAC/SMA* | 55 | 85 | 30 | 4.6 | 2.8 | 0% | — | — |
| 13 | Control | — | — | — | — | — | — | 66 | 251 |
| 14 | Gafquat® | — | — | — | — | — | — | 182 | 230 |

*SMA is stearyl methacylrate ($C_{18}$ acrylate)

Examples 15–21

Various terpolymers and a copolymer were synthesized to further demonstrate the instant invention. These samples were evaluated for wet comb and detangling vs. a no polymer control and Gafquat® HS-100 in each of these formulations. The results of these evaluations are shown in Tables 4 and 5 below.

Conditioner. This polymer was tested for detangling and wet comb versus a control (no polymer) and Gafquat® HS-100 in each of these formulations. The results of these evaluations are shown in Tables 4 and 5 below.

TABLE 4

| | Total Work (mJ) | | |
|---|---|---|---|
| | Control | Gafquat ® | AA/MAPTAC/MA |
| Detangling | | | |
| Shampoo #1 | 352 | 256 | 433 |
| Shampoo #2 | 357 | 315 | 126 |
| Conditioner | 116 | 14 | 27 |
| Wet Comb | | | |
| Shampoo #1 | 199 | 67 | 32 |
| Shampoo #2 | 127 | 78 | 31 |
| Conditioner | 84 | 25 | 22 |

It can be seen in the detangling results that the AA/MAPTAC/MA polymer performs substantially better than Gafquat HS-100 in shampoo #2. The wet comb results reveal that this polymer performs better in all three formulas.

Example 23

Silkening Showering Gel

| | Ingredients | % W/W |
|---|---|---|
| A | Deionized Water | q.s. to 100 |
| | Standapol ES-3[1] | 35.0 |
| | Tegobetaine C[2] | 10.0 |
| | Mirataine CBS[3] | 10.0 |
| B | Hamposyl L-30[4] | 5.0 |
| | 45/45/10 AA/MAPTAC/MA | |
| C | Tetrasodium EDTA | 0.2 |
| | Fragrance, | q.s. |
| | Preservative, and color | |
| | Citric Acid | q.s. to pH 6.0 |

Preparation

A silkening shower gel was prepared as follows: the ingredients of Part A were mixed in the order listed, proceeding sequentially after each addition became clear and uniform. Sodium lauroyl sarcosinate and the AA/MAPTAC/MA polymer were added as Part B. During continued mixing, Part C was added and the pH was adjusted to 6.0 with citric acid.

This method resulted in a mild shower gel having excellent flash foam properties and excellent slip to the lather. Use of this gel left skin feeling silky smooth. Indexed ingredients commercially available from:
1. Henkel, Inc.
2. Goldschmidt Chemical Co.
3. Miranol Chemical Co.
4. W. R. Grace

Example 24

Moisturizing Night Cream

| | Ingredients | % W/W |
|---|---|---|
| A | Adol 52[1] | 5.00 |
| | Ceraphyl 424[1] | 5.00 |
| | Liponate IPP[3] | 5.00 |
| | Acetulan[4] | 2.50 |
| | Arlacel 60[5] | 3.00 |
| | Tween 60[5] | 2.60 |
| | Blandol[6] | 1.00 |
| | Refined Paraffin Wax[7] | 0.50 |
| | White Ceresine Wax[7] | 0.75 |
| B | Deionized Water | q.s. to 100 |
| | Butylene Glycol | 2.00 |
| | Glucam E-20 | 1.00 |
| | Triethanolamine 99% | 0.10 |
| C | 45/45/10 AA/MAPTAC/MA | 3.50 |
| D | Fragrance and Preservative | q.s |

Preparation

A moisturizing night cream was prepared by mixing parts A and B in separate vessels, heating each to 78° C., and slowly adding Part A to Part B with stirring. Mixing was continued and cooling permitted when uniform. Part C was then added at 50° C., with continued mixing and cooling. Part D was then added at 40° C. with continued cooling and mixing. Pouring occurred at 30° C.

This method resulted in a rich night cream, which had excellent substantivity, softness, feel and moisturizing properties. Indexed ingredients are commercially available from:
1. Sherex Chemical Co.
2. Van Dyk & Co., Inc.
3. Lipo Chemicals, Inc.
4. Amerchol Corp.
5. ICI Americas
6. Witco Sonneborn Div.
7. Strahl & Pitsch, Inc.

Example 25

Hydroalcohol Suntan Lotion

| | Ingredients | % W/W |
|---|---|---|
| A | Deionized Water | q.s. to 100 |
| | 45/45/10 AA/MAPTAC/MA | 3.50 |
| B | SD Alcohol | 59.00 |
| | Octyl Dimethyl PABA | 5.00 |
| | PEG-12 | 4.75 |
| | C12–15 Alcohol | 4.75 |
| | Coconut Fragrance BL-08[1] | 0.10 |

Preparation

Parts A and B were prepared in two separate vessels. With moderate agitation, Part B was added into Part A. Mixing continued until clear and uniform. Indexed ingredients are commercially available from:
1. Novarome Inc.

This method resulted in a lotion with excellent skin moisturization and feel properties.

Example 26

Moisturizing Hand Lotion

| | Ingredient | % W/W |
|---|---|---|
| A | Adol 52[1] | 5.0 |
| | Ceraphyl 424[2] | 5.0 |
| | Glucate SS[3] | 0.8 |

-continued

| Ingredient | % W/W |
|---|---|
| Liponate IPM[6] | 4.0 |
| Arlacel 60[4] | 3.0 |
| Tween 60[4] | 2.6 |
| White Ceresine Wax[5] | 0.4 |
| B Deionized Water | 76.25 |
| Glucamate SSE-20[3] | 1.50 |
| 45/45/10 AA/MAPTAC/MA | 1.25 |
| Triethanolamine 99% | 0.20 |
| C Fragrance and Preservative | q.s. |

Preparation

Part A was heated to 78° C. In a separate vessel, the ingredients of Part B were added to water and heated to 80° C. Slowly, Part A was added into Part B with stirring. Cooling began when uniform. Part C was added at 40° C., with continued mixing and cooling. The product was poured at 30° C. Indexed components are commercially available as follows:

1. Sherex Chemical Co.
2. Van Dyk Co., Inc.
3. Amerchol Corp.
4. ICI Americas
5. Strahl & Pitsch, Inc.
6. Lipo Chemicals, Inc.

Example 27

Hand and Body Lotion

| | Ingredients | INCI NAME | % W/W |
|---|---|---|---|
| Part A | DI Water | DI Water | q.s. to 100 |
| | Carbomer | Carbopol 940 | 0.20 |
| Part B | Glucate SS | Methyl Glucose Sesquistearate | 0.80 |
| | Glucamate SSE-20 | PEG-20 Methyl Glucose Sesquistearate | 1.00 |
| | Acetulan | Cetyl Acetate & Lanolin Alcohol | 2.00 |
| | Promulgen D | Cetearyl Alcohol and Ceteareth-20 | 2.00 |
| | Cerasynt SD | Glyceryl Monostearate | 0.50 |
| | Blandol | Mineral Oil | 8.00 |
| Part C | TEA 99% | TEA 99% | q.s. to pH7 |
| Part D | 45/45/10 AA/MAPTAC/AA | 45/45/10 M/MAPTAC/MA | 3.00 |
| | Preservative | Gyldant | 0.075 |
| | Fragrance | | q.s. |

Preparation

DI water was heated to 80° C., and Carbomer was sifted in slowly. Mixing occurred until the Carbomer was hydrated while maintaining temperature. Part B was then treated to 80° C. With rapid agitation, Part B was added to Part A. These components were then mixed for 15 minutes while maintaining temperature. 99% TEA was then added to neutralize. Mixing was then initiated with cooling. At 40° C., Part D was added, and mixing continued until uniform and at room temperature.

Example 28

Soap Bar

| Ingredients | % W/W |
|---|---|
| Soap Base* | 98.325 |
| Sodium Silicate (liquid - 37.43%) | 0.400 |
| Tetrasodium EDTA | 0.025 |
| Titanium Dioxide | 0.250 |
| 45/45/10 AA/MAPTAC/MA | 1.000 |

*80/20 Tallow-coconut fatty acid, sodium salt

Preparation

The 45/45/10 AA/MAPTAC/MA was added to the noodles in the amalgamator and a small amount of water was misted onto the batch to assist in the hydration of the polymer.

Example 29

Neutralizing Shampoo

| | Ingredients | INCI Name | % W/W |
|---|---|---|---|
| A | DI Water | Water | q.s. |
| | Standapol A[1] | Ammonium lauryl sulfate | 30.0 |
| | Standapol EA-2[1] | Ammonium lauryl sulfate | 18.0 |
| | Varsulf SBFS-30[2] | Disodium laureth sulfosuccinate | 8.0 |
| | Tegobetaine L-7[3] | Cocamidopropyl betaine | 3.0 |
| | Monamid 1113 | Cocamide DEA | 0.5 |
| B | EGDS-VA[3] | Ethylene glycol distearate | 2.0 |
| | Adol 52[5] | Cetyl Alcohol | 2.0 |
| C | Polymer of instant invention | 45/4511 0 AA/MAPTAC/MA | 2.0 |
| | Merguard 1200[6] | Methldibromo Glutaronitrile and Phenoxyethanol | 0.2 |
| | Fragrance | Fragrance | q.s. |
| | Phosphoric Acid | Phosphoric Acid | q.s. to pH 5 |

Preparation

Parts A and B were prepared in separate vessels and heated to 70° C. while mixing. Part B was combined with Part A with continuous mixing while cooling. At 40° C. Part C was added and mixed until uniform. Indexed ingredients are commercially available from:

1. Henkel Corporation
2. Witco Corporation
3. Goldschmidt Chemical Corporation
4. Mona Industries, Inc.
5. Proctor & Gamble Chemicals
6. Calgon Corporation Example 30

Cream Hair Relaxer

| | Ingredients | INCI Name | % W/W |
|---|---|---|---|
| A | Carnation mineral oil[1] | Mineral Oil | 5.0 |
| | Alba Protopet[1] | Petrolatum | 10.0 |
| | Cyclochem NI[2] | Cetearyl Alcohol and Ceteareth-20 | 20.0 |

| Ingredients | INCI Name | % W/W |
|---|---|---|
| B DI Water | Water | q.s. to 100 |
| NaOH (50%) | Sodium Hydroxide | 3.0 |
| C Polymer of instant invention | 45/45/10 AA/MAPTAC/AA | 2.5 |
| Merguard 1200[3] | Methyldibromo Glutaronitrile and Phenoxyethanol | 0.2 |
| Fragrance | Fragrance | q.s |

Preparation

Parts A and B were prepared in separate vessels and heated to 70° C. while mixing. Part A was combined with Part B during continued mixing while cooling. At 40° C., Part C was added and mixed until uniform. Indexed ingredients commercially available from:
1. Witco Corporation
2. Rhone-Poulenc
3. Calgon Corporation

What is claimed is:

1. An ampholyte polymer comprising:
   a) about 25 to about 75 mol % APTAC or MAPTAC, alone or in combination;
   b) about 25 to about 75 mol % acrylic acid, methacrylic acid, AMPSA or MAMPSA, alone or in combination; and
   c) about 0.1 to about 20 mol % of a $C_1$–$C_{22}$ straight or branched chain alkyl acrylate or methacrylate.

2. The polymer of claim 1, wherein said alkyl acrylate is methyl acrylate.

3. A cosmetically acceptable medium containing from about 0.1 to about 20%, based on the weight of said medium, of the polymer of claim 1.

4. The polymer of claim 1, wherein a) is MAPTAC and b) is acrylic acid.

5. The polymer of claim 1, wherein the molecular weight ranges from about 100,000 to about 10,000,000.

* * * * *